US00PP23250P2

(12) United States Plant Patent
Hornig

(10) Patent No.: US PP23,250 P2
(45) Date of Patent: Dec. 11, 2012

(54) ***CENTAUREA* PLANT NAMED 'BLACK SPRITE'**

(50) Latin Name: *Centaurea montana*
Varietal Denomination: Black Sprite

(76) Inventor: Ellen Hornig, Oswego, NY (US)

( * ) Notice: Subject to any disclaimer, the term of this patent is extended or adjusted under 35 U.S.C. 154(b) by 31 days.

(21) Appl. No.: 13/134,941

(22) Filed: Jun. 21, 2011

(51) Int. Cl.
*A01H 5/00* (2006.01)
(52) U.S. Cl. ..... Plt./263.1
(58) Field of Classification Search ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Centaurea* named 'Black Sprite' characterized by its short, compact plant habit and its inflorescences that are dark purple-black in color with outer florets petals that are long, narrow, and spidery.

2 Drawing Sheets

Botanical classification: *Centaurea montana.*
Variety denomination: 'Black Sprite'.

BACKGROUND OF THE INVENTION

The present invention relates to a new and distinct cultivar of *Centaurea montana*. The new cultivar will be referred to hereafter by its cultivar name, 'Black Sprite'. 'Black Sprite' is a new herbaceous perennial grown for landscape use.

The inventor discovered the new cultivar, 'Black Sprite', as a naturally occurring whole plant mutation in Oswego, N.Y. in summer of 2006 that arose from self-pollination of *Centaurea* 'Black Widow' (not patented).

The new cultivar was first asexually propagated by the inventor by division in Oswego, N.Y. in spring of 2008. Asexual propagation has determined that the characteristics of this cultivar are stable and are reproduced true to type in successive generations.

SUMMARY OF THE INVENTION

The following traits have been repeatedly observed and represent the characteristics of the new *Centaurea* as observed for a period of four years in Oswego, N.Y. These attributes in combination distinguish 'Black Sprite' as a unique cultivar of *Centaurea.*

1. 'Black Sprite' exhibits inflorescences that are dark purple-black in color.
2. 'Black Sprite' exhibits inflorescences in which the outer florets have petals that are long, narrow, and spidery.
3. 'Black Sprite' exhibits a short, compact plant habit.

The new cultivar of *Centaurea* can be readily distinguished from its parent plant and other cultivars. 'Black Widow' differs from 'Black Sprite' in having inflorescences that are dark purple but less black in color, in having a taller and less compact plant habit, and in being less mildew resistant. 'Black Sprite' can be compared to the cultivar 'Dot Purple' (not patented), the parent plant of 'Black Widow'. 'Dot Purple' differs from 'Black Sprite' in having purple flowers (not black-purple). 'Black Sprite' can also be compared to the typical plants of the species *Centaurea montana*, which differ from 'Black Sprite' in having blue-purple flowers, a less compact plant habit, and broader floret petals.

BRIEF DESCRIPTION OF THE DRAWING

The accompanying colored photographs illustrate the overall appearance and distinct characteristics of the new *Centaurea*, 'Black Sprite', as grown outdoors in a garden in Oswego, N.Y. The photographs were taken in early summer plants of plants about two years in age.

DETAILED BOTANICAL DESCRIPTION

Figure 1:
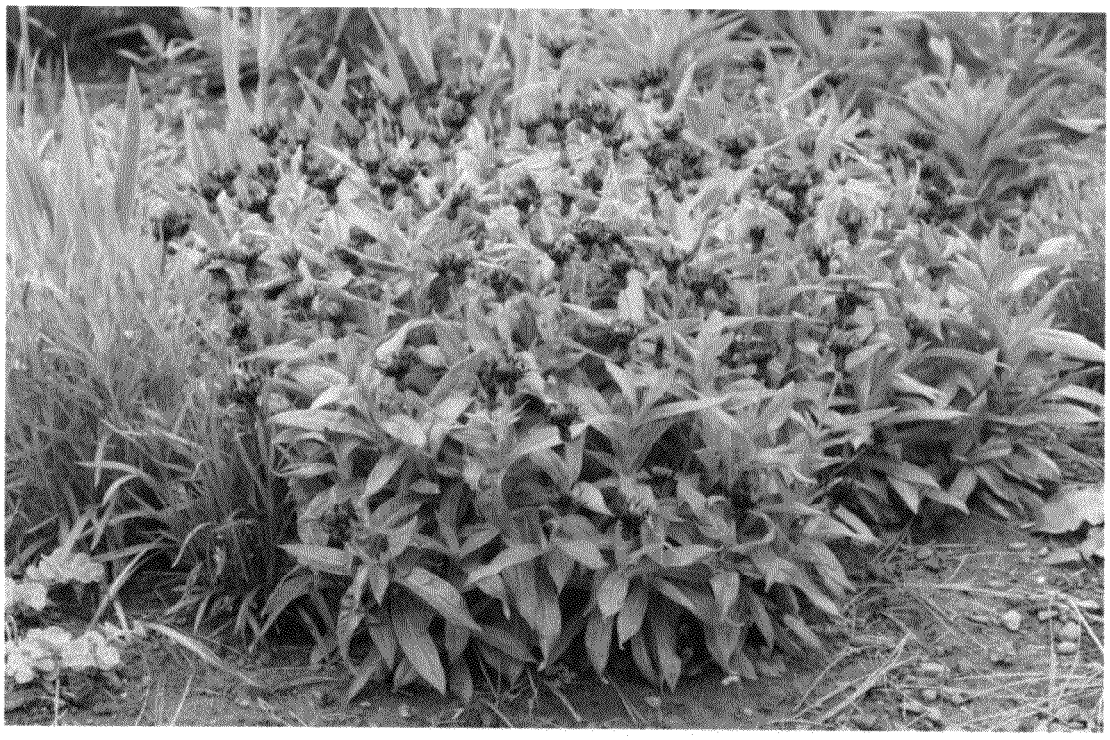
FIG. 1 and FIG. 2 provide a view of plants of 'Black Sprite' in bloom and illustrates its compact plant habit.
Figure 2:
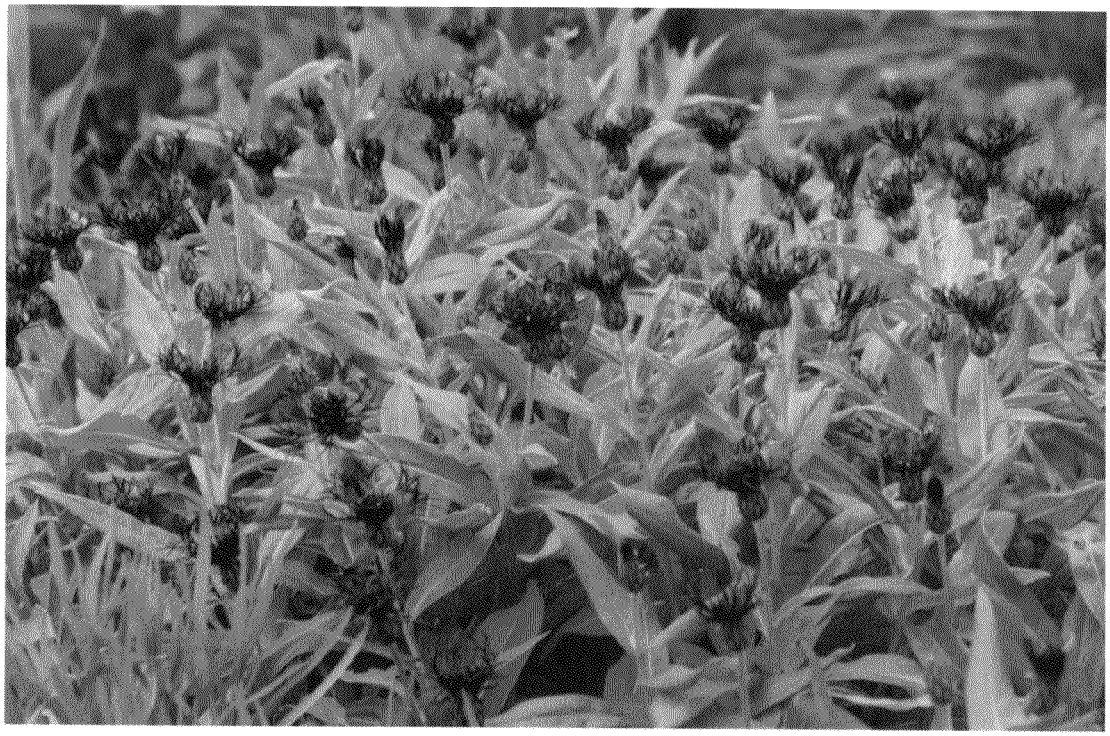
Figure 3:
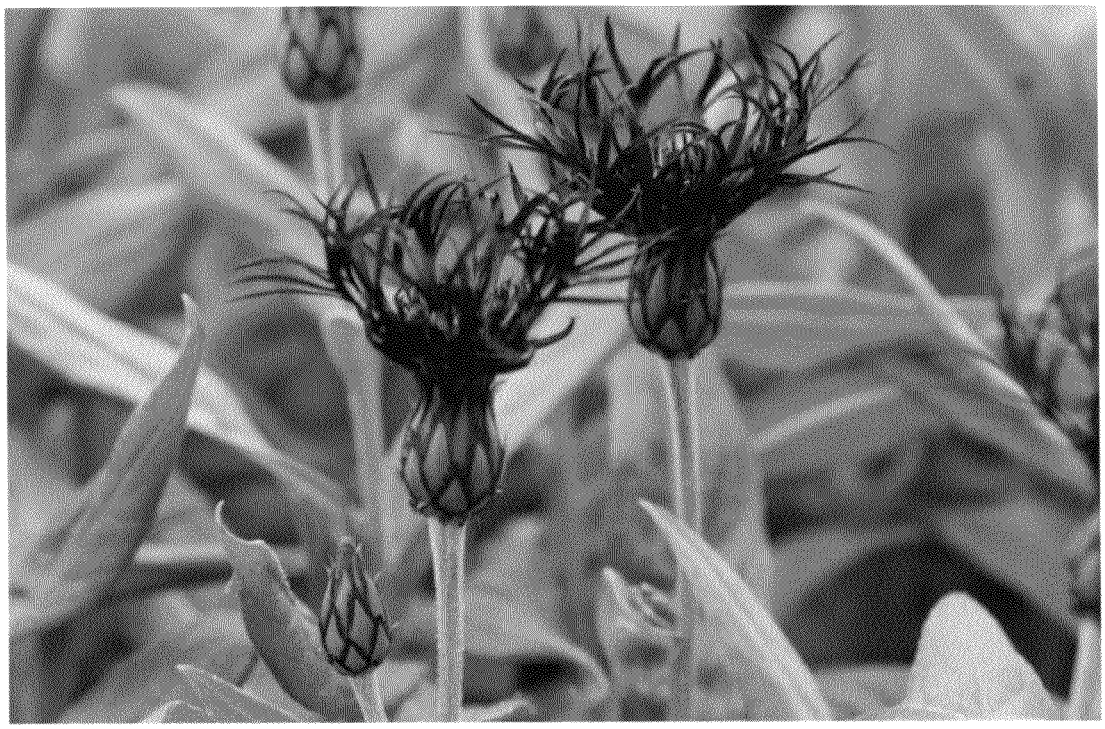
FIG. 3 provides a close-up view of inflorescences of 'Black Sprite' and FIG. 4 provides a close-up view of the spidery floret petals of 'Black Sprite'. The colors in the photographs are as close as possible with the digital photography and printing techniques utilized and the color codes in the detailed botanical description accurately describe the new *Centaurea.*
Figure 4:
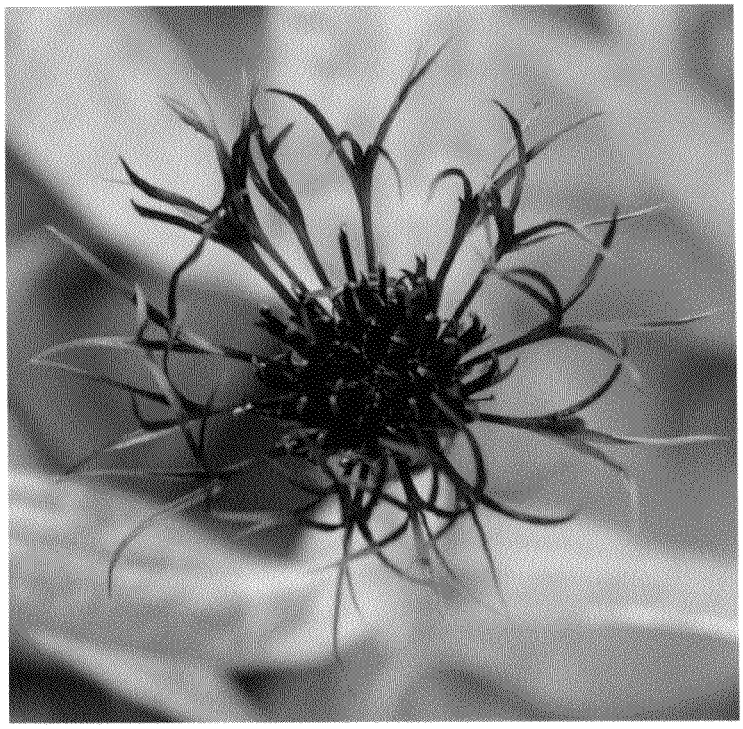

The detailed botanical data was collected on plants about one year in age as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—About 3 weeks in early summer, will re-bloom periodically if sheared back after bloom.

*Plant habit.*—Compact upright mound, slowly spreading.

*Height and spread.*—About 24 cm in height and 20 cm in width (one-gallon container).

*Cold hardiness.*—At least in U.S.D.A. Zone 5.

*Diseases and pests.*—Some resistance to powdery mildew has been observed.

*Propagation.*—Division and basal cuttings.

*Growth rate.*—Moderate

*Roost.*—Fibrous.

Branch description:

*Stem shape*.—Oval.

*Stem color*.—144A.

*Stem surface*.—Tomentose with most covered with decurrent leaves.

*Branching*.—Basal branches, an average of 16 as grown in a one-gallon container.

*Stem size*.—An average of 20 cm in length (including peduncles) and 4 mm in width.

Foliage description:

*Leaves*.—Alternate arrangement, oblanceolate in shape, attachment deccurent with blade portion cuneate, acuminate apex, entire margin, pubescent on upper surface and lower surface, up to 15 cm in length and 3.5 cm in width, not fragrant, color of upper surface; a blend of 144A and 137B, color of lower surface; a color between 138A and 138B, venation; pinnate, non conspicuous, 146B in color on upper surface and 146C in color on lower surface.

Inflorescence description:

*Inflorescence type*.—Semihemispheric, comprised of a center area of fertile shorter florets and an outer row of sterile, long, narrow, spidery florets.

*Inflorescence number*.—1 per stem, about 14 as grown in a one-gallon container.

*Inflorescence fragrance*.—None.

*Inflorescence size*.—Average of 3.8 cm in depth and 5 cm in diameter.

*Peduncles*.—Oval in shape, an average of 5.7 cm in length and 3 mm in diameter, surface is tomentose, color 144B.

*Bracts*.—About 28 arranged in about 5 overlapping rows forming a conical structure, range from 7 mm to 1.8 cm in length and an average of 4 mm in width, ovate to lanceolate in shape, surface is glabrous on upper and lower surface, margin on outer bracts are feathered and margins on inner bracts are entire, acute to acuminate apex, color of upper surface is 137A with veins 144b in color, color of outer and inner surface is a blend of 144A and 143A with the upper portion of the inner bract suffused with N77B with margins N186A.

*Floret number*.—An average of 14 outer florets and an average of 24 inner florets.

*Flower buds*.—Conical in shape, comprised of overlapping bracts, an average of 2 cm in length and 1 mm in width, 144A in color with margins of bracts 202A, surface is glabrous with margins of triangles feathery.

*Inflorescence longevity*.—5 to 7 days.

*Floret type*.—Tubular.

*Outer florets*.—An average of 3.7 cm in length and 1.4 cm in width, comprised of 5 tepals that spread outward near apex (limbs) and are fused into tube, tube portion is an average of 23 cm in length and 1 mm in width, un-fused limbs are an average of 1.3 cm in length and 1 mm in width, linear in shape, entire margins, acuminate apex, color of limbs is a blend of N77A and N186A, color of tube is a blend of N77A and N186A with base (covered by bracts) NN155B, all surfaces are glossy and very sparsely pubescent, sterile.

*Inner florets*.—An average of 2.3 cm in length and 3 mm in width, comprised of 5 tepals fused into a tube with limbs held upright, tube portion is an average of 1.2 cm in length and 1 mm in width, limbs are an average of 1.1 cm in length and 1 mm in width, linear in shape, entire margins, acuminate apex, color of limbs a blend of N77A and N186A, color of tube is a blend of N77A and N186A with base (covered by bracts) NN155B, all surfaces are glossy and very sparsely pubescent.

Reproduction organs (present on inner florets only):

*Pistil*.—1, stigma is bifid with limbs an average of 1 mm in length and N79A in color, style is an average of 1.8 cm in length and N79A in color becoming NN155B at base, ovary is oblong in shape, about 2 mm in length and 1.5 mm in width and 155B in color.

*Stamens*.—5, filaments are about 1.8 cm in length and N79A in color, anthers are fused into tube surrounding pistil, an average of 1 mm in width and 5 mm in length, N186A in color, pollen was not observed.

*Seeds*.—Not observed on the plants available for data collection, likely to be produced under the right environmental conditions.

It is claimed:

1. A new and distinct cultivar of *Centaurea* plant named 'Black Sprite' as herein illustrated and described.

* * * * *